(12) United States Patent
Iversen et al.

(10) Patent No.: US 7,942,935 B2
(45) Date of Patent: May 17, 2011

(54) DEVICE AND SYSTEM FOR PROSTHETIC KNEES AND ANKLES

(75) Inventors: Edwin Kay Iversen, Salt Lake City, UT (US); Harold H. Sears, Salt Lake City, UT (US); Arthur D. Dyck, Draper, UT (US); Steven R. Kunz, Salt Lake City, UT (US); Joseph Anthony Jacobs, Salt Lake City, UT (US); James R. Linder, West Jordan, UT (US); Peter K. Strazdins, Park City, UT (US)

(73) Assignee: Motion Control, Salt Lake City, UT (US)

( * ) Notice: Subject to any disclaimer, the term of this patent is extended or adjusted under 35 U.S.C. 154(b) by 804 days.

(21) Appl. No.: 11/394,331

(22) Filed: Mar. 29, 2006

(65) Prior Publication Data

US 2006/0235544 A1 Oct. 19, 2006

Related U.S. Application Data

(60) Provisional application No. 60/666,388, filed on Mar. 29, 2005.

(51) Int. Cl.
*A61F 2/70* (2006.01)

(52) U.S. Cl. ......................................... 623/25

(58) Field of Classification Search ............... 623/25, 623/47, 24, 26
See application file for complete search history.

(56) References Cited

U.S. PATENT DOCUMENTS

| | | | |
|---|---|---|---|
| 1,051,288 A * | 1/1913 | Szydlowski | 188/309 |
| 3,820,168 A * | 6/1974 | Horvath | 623/24 |
| 3,883,900 A * | 5/1975 | Jerard et al. | 623/25 |
| 5,704,945 A * | 1/1998 | Wagner et al. | 623/44 |
| 5,957,981 A * | 9/1999 | Gramnas | 623/47 |
| 6,106,560 A * | 8/2000 | Boender | 623/44 |
| 6,187,052 B1 | 2/2001 | Molino et al. | |
| 6,443,993 B1 | 9/2002 | Koniuk | |
| 6,764,521 B2 | 7/2004 | Molino et al. | |

* cited by examiner

*Primary Examiner* — Corrine M McDermott
*Assistant Examiner* — Melissa Hoban
(74) *Attorney, Agent, or Firm* — Thorpe North & Western LLP (57) ABSTRACT

A device and system is provided for a prosthetic device having an articulating joint for a leg amputee. The device includes a joint housing forming a chamber, and the chamber has a first opening. A rotary hub can be disposed within the joint housing and configured to act as the articulating joint. One or more vanes can extend outwardly from the rotary hub, and the vane is configured to actuate fluid flow through the first opening.

23 Claims, 9 Drawing Sheets

DEVICE AND SYSTEM FOR PROSTHETIC KNEES AND ANKLES

Priority of U.S. Provisional patent application Ser. No. 60/666,388 filed on Mar. 29, 2005 is claimed.

FIELD OF THE INVENTION

The present invention relates generally to prosthetic devices.

BACKGROUND

An intact human foot, connected to its ankle, travels through stance and swing phases of a gait cycle during each stride of motion, whether the motion involves walking, jogging, or running. By adjusting the stiffness and damping characteristics of a prosthetic ankle or knee mechanism, the springiness of the intact natural human foot and its corresponding natural human joints may be mimicked, thereby optimizing the prosthetic for the desired motion of the wearer. The characteristics that are desired to store and release energy appropriately for walking tend to oppose those best suited to fast walking and running.

In a stance phase, the foot is in contact with the ground and the weight of a person is supported on the foot. In a swing phase, the foot is off the ground as the entire leg and foot move from a posterior position to an anterior position with respect to a center of gravity of the person.

Figure 1:
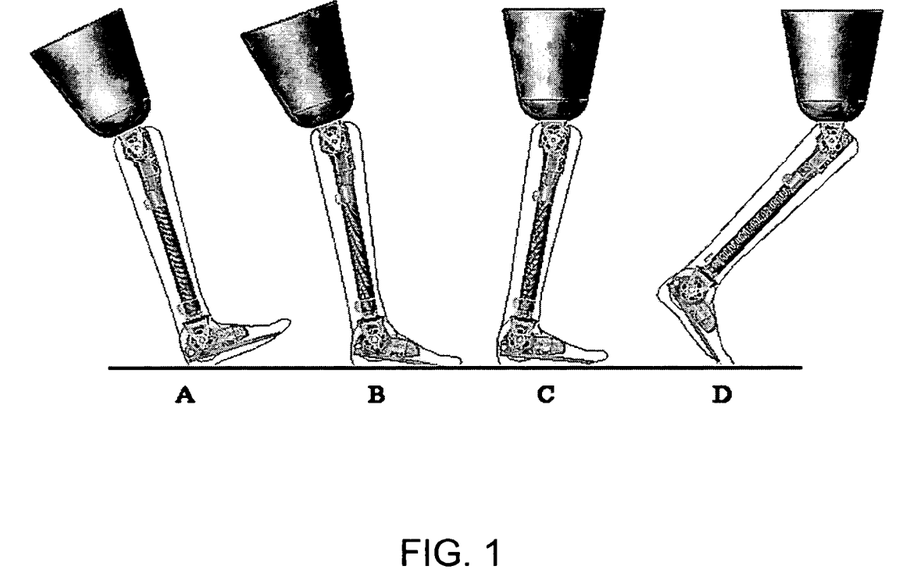
FIG. 1 is an illustration showing the stance phase features of a knee/ankle prosthetic system.

The stance phase A, as shown in FIG. 1, begins just after completion of the swing phase and commences with a heel strike wherein the foot is lowered to the ground as the body moves forward from a position posterior to the person's center of gravity. Immediately after heel strike, the foot moves from a dorsi-flexed position, wherein the toes of the foot are pointed upwards, to a plantar-flexed position B wherein the bottom of the foot or shoe is flat on the walking surface, which provides greater stability as the entire weight of the person is shifted over the foot in contact with the ground.

The swing phase C commences just after heel strike of the other foot. During the swing phase, the foot is again in the dorsi-flexed position D as the foot leaves the walking surface and the foot and leg swing forward in preparation for the stance phase. Dorsi-flexion is important for normal human locomotion, since the toes are dorsi-flexed in order to clear the floor. If the foot is not dorsi-flexed during the swing phase, it would most likely catch on the walking surface and cause the person to stumble and fall, which may lead to serious injury.

It is beneficial for the joint mechanism of a prosthetic ankle to have the ability to resist plantar flexion at heel strike and to store energy during dorsi flexion/extension. During the swing phase, lifting the toe is also desirable. If the dynamic response is too stiff, the foot bounces back too quickly. If the spring is too soft, it stores less energy and releases too late. Similar considerations apply in the case of such a prosthetic joint acting in the role of a knee, and the mechanical coupling of these two joints acting in combination complicates the creation of a solution which is satisfactory throughout the range of motion.

There are prosthetic ankle joints currently available which are designed to assist a user during walking or travel through stance and swing phases of a gait cycle. Prior prosthetic devices have difficulty efficiently accommodating a combination of slopes in sideward fashion that act upon the bottom of the foot during travel by an amputee. The movements of the human foot are so complex, that even sophisticated prosthetic devices do not imitate many important aspects of the human ankle movement during walking. In this respect, the available prosthetic ankle joints are not fully capable of movement from side to side, which is needed to encompass the required range of movements of the human ankle in inversion and eversion positions accompanied by the controlled return thereof to the medial or neutral position.

There are known multi-axial ankle joints seeking to mimic those aforementioned actions of the ankle as the foot comes into contact with the ground surface attaining the instantaneous inversion/eversion and medial/neutral geometries through the motion. However, such devices do not capitalize on certain dynamic characteristics of the motion of the ankle joint in combination with the knee joint during the periods of plantar flexion and dorsi-flexion.

Other prior art joints do not adequately address the problems amputees face in getting lower limb prostheses to behave more like the original equipment. Simplistic joint designs exhibit a simplistic relationship between external influence and behavior of the knee joint. Specifically, while the joint is unloaded over the swing phase, the joint maintains itself in a locked status, and conversely, when loaded on stance phase initiation, it toggles to unlocked mode. This bi-polar mode shift regimen of control does not effectively serve a user's range of possible needs across different gait scenarios. Moreover, the absence of a regulated impedance aspect as part of the control regimen for this design fails to address such persistent issues as the tendency of the lower limb to essentially kick the user's posterior at the culmination of swing phase, and the impact suffered at the terminal point of each swing phase in gait.

Some knee-joint focused designs rely on a toe-loading moment to exceed a given threshold level before the knee joint is enabled to go into locked mode. This means initiation is subject to a potential of premature or latent knee joint mode shift under certain exigencies of the terrain being navigated by a user.

The action of a human knee joint requires less mechanism complexity in replication than that of the ankle, because it is essentially a hinge, but coordinating its dynamic response characteristics to suitably match those of the ankle joint, over the range of intended cadence is challenging. The knee mechanism should have the ability to exhibit high resistance to bending and compliance during stance phase. Simultaneously, the mechanism will desirably dissipate energy and store then release energy.

Furthermore, there are several other problems limiting the success of attempts in producing lower limb prosthetic devices. Maintaining compactness of the ankle joint to match dimensions of variably sized shoes has traditionally been a design obstacle. Similarly, issues surrounding the relationship between mechanical stress generated as a result of shear force and bending acting along the principal hinge axis exceeding material strength limits create engineering challenges. In addition, there is the need to minimize component wall thicknesses and lateral dimensions across the joint.

SUMMARY OF THE INVENTION

A device and system is provided for a prosthetic device having an articulating joint for a leg amputee. The device includes a joint housing forming a chamber, and the chamber has a first opening. A rotary hub can be disposed within the joint housing and configured to act as the articulating joint. One or more vanes can extend outwardly from the rotary hub, and the vane is configured to actuate fluid flow through the first opening.

Additional features and advantages of the invention will be apparent from the detailed description which follows, taken in conjunction with the accompanying drawings, which together illustrate, by way of example, features of the invention.

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention includes an energy storing prosthetic device that may have controlled impedance in an electro-hydraulic multi-axis prosthetic knee or ankle This controlled-impedance transfemoral prosthesis device can include a hydraulic ankle, coupled to an energy storing foot via an elastomeric interface. A limb-like link can be included that is a hydraulic knee mounted by a prosthetic socket to the amputee patient's remnant limb as desired. Both the ankle and knee devices may be electronically controlled or mechanically controlled, together or separately. The control can be obtained by adjusting the dynamic characteristics of either one or both joints, such as the stiffness and damping of the mechanism's response to motion imparted from or demanded by the amputee.

In an exemplary embodiment, a prosthetic lower limb system unit is provided which is capable of imitating important dynamic characteristics, including spring stiffness and damping of the movements of the human ankle and knee joints during motion of the patient user ranging from walking through running.

Figure 2:
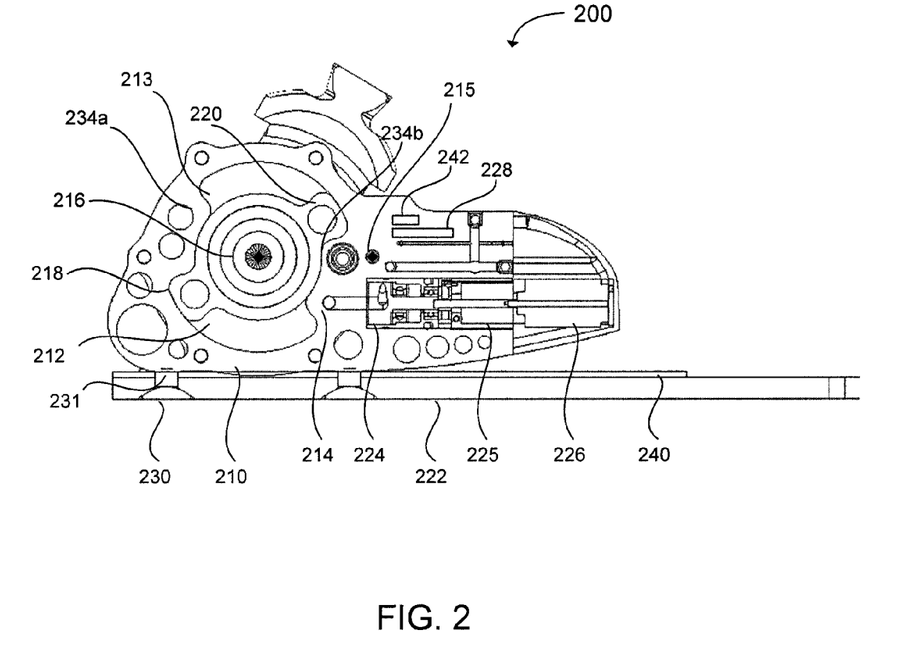
FIG. 2 is a cross-sectional side view of a prosthetic foot system with an electronically controlled hydraulic damping system in an embodiment of the invention.

The prosthetic device 200 can have an articulating joint for a leg amputee. Both the knee and ankle can use the hydraulic joint that will be described. However, FIG. 2 illustrates an ankle embodiment.

A joint housing 210 is provided and forms a first chamber 212. The first chamber can have a first opening 214 that allows hydraulic fluid to pass through it. A rotary hub 216 is disposed within the joint housing and is configured to act as the articulating joint. The rotary hub may be a rotating shaft bearing. The bearings may be high load needle bearings that are convoluted internal to the rotary hub to minimize width and provide an extremely strong ankle bearing. Alternatively, the ankle may rotate around this hub axis or rotary axle using some other type of bearings (e.g., ball bearings). In one embodiment, a rotary actuator is the combination of the joint housing, rotary hub and vane(s). By placing the bearings internal to the rotary hub, the moments on the vanes are reduced and this allows lighter construction materials to be used for the bearing.

A vane 218 can extend outwardly from the rotary hub 216. The vane is configured to actuate fluid flow through the first opening 214. This provides hydraulic resistance to the toe keel element 222 and joint body or housing 210. The first opening can lead to a fluid passageway that has flow elements, venturi structures, and/or valves stationed along the passage which restrict fluid flow under certain conditions or cause it to be diverted to other sub-branches of the passageway.

In addition, check valves can be coupled to the fluid flow in the fluid passageway or sub-passage way to allow the passage of fluid in one direction but not in the other. The fluid passageway can allow fluid to flow in a certain direction corresponding to rotary hub motion subtending plantar-flexion motion of the prosthetic joint, and conversely, allow fluid to flow in the opposing direction corresponding to rotary hub motion subtending dorsi-flexion motion of the prosthetic joint. This allows the length of path traveled by the fluid when it flows in one direction to be equal to that traveled when the fluid flows in the opposite direction.

The employment of a rotary action vane-type actuator at each joint has important advantages over use of one or more linear piston-type actuators to serve each joint, like those primarily observed in prior art. Rotary actuation accommodates a range of flexion angulation (at least 104 degrees) which exceeds what is achievable with a linear actuator when combined with its necessary linkages, particularly in the very limited space that is available in a prosthetic application.

The nature of the vane action rotating in a chamber of circular cross-sectional profile (when viewed from the side) equalizes the supply versus return fluid path lengths, which tends to balance the internal fluid viscous/friction forces, and thereby directly allows the load to be balanced. This is also a significant advantage in terms of minimizing effort the amputee must input to overcome overhead created by design element motion.

The prosthetic system can have an ankle joint with a sufficiently small size to enable it to fit within typical shoe sizes. The reduced size can be accomplished by the rotary hydraulic actuator allowing a vane-like element having pressure surfaces of a sufficiently generous area to keep working fluid pressures below unfeasible threshold values.

The toe keel element 222 may be coupled to the bottom side of the joint housing 210 with a single pivot point coupling 230, to enable a restricted rotation of the toe keel about the device axis. Alternatively, the toe keel element may be mounted on a spherical or cylindrical surface in order to rotate and facilitate resistance to eversion or inversion. When the toe keel is coupled to the joint housing, this allows the toe keel to store and release energy during the third rocker portion of the stance gait cycle.

Although intended to mimic the natural anatomy, field testing has demonstrated that more lateral roll can contribute to an amputee's stumbling due to the user stepping on a ground protruding obstacle. Mitigating the initial restore-to-center-upright moment action is valuable, and this permits a relatively relaxed hinge or spherical joint connection to be used where resistance to deflection becomes significant, and the deflection is felt by the user only once this deflection grows to a significant angular deviation from neutral. Thus, a user, who feels an obstacle underfoot, does not experience an upper torso de-stabilizing moment, which is the reaction to the moment induced when a strong restore-to-centre-upright moment is initiated between the body of the ankle joint (foot) and its base-plate (keel). The use of a spherical or cylindrical surface reduces the tendency for stumbling on the limb, which is undergoing the course of stance phase contact.

Figure 3:
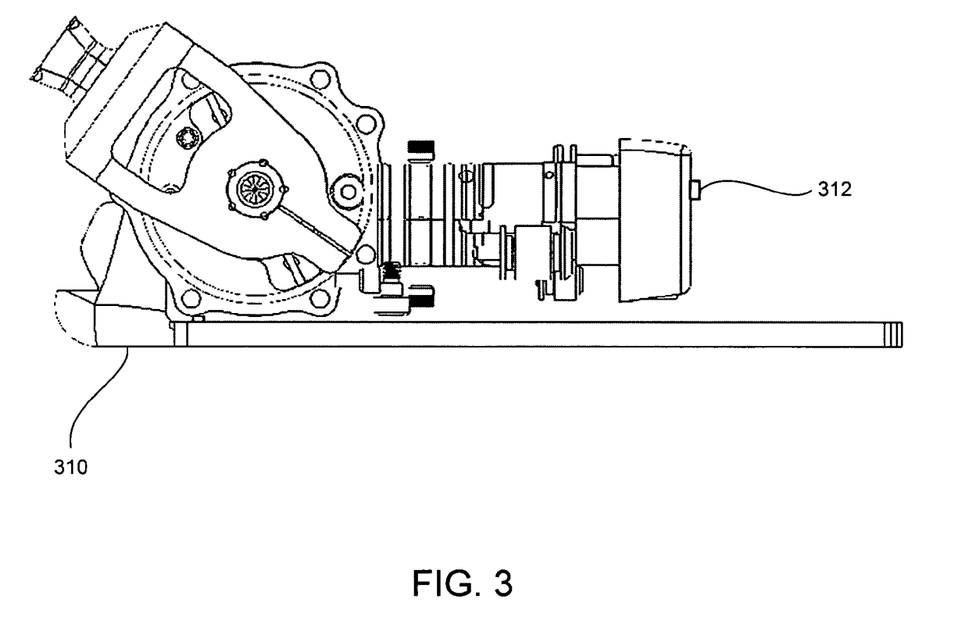
FIG. 3 is an illustration of a prosthetic foot system having an elastomeric member for use in lower limb replacement, in accordance with an embodiment of the present invention.

FIG. 3 illustrates that a valuable complement for the invention embodiments is an interchangeable heel element 310 which is integral to providing the compliance of the connection between the foot and keel. Attached, perhaps, by simple fasteners to a posterior/underside tending surface of the foot, this piece has features which allow it to mate with rearward located projections on the keel, maintaining the keel in its regular orientation, yet facilitating the shallow restore-to-centre-upright characteristic, in the case of deflection in any rotational degree of freedom, as described.

A suitably chosen material for this heel piece will also permit it to satisfactorily absorb shock at each heel contact, offer some wear resistance, but also be a readily disposable and replaceable item during refurbishment of a worn prosthesis. For example, an elastomeric heel element can be coupled to the joint housing to provide shock absorption during a heel strike.

To enable a prosthetic device to behave more naturally, energy associated with plantar flexion and dorsi-flexion motion of the ankle joint in combination with the knee joint can be momentarily stored and released. When the energy is stored and released in synchronization with the cadence of a prosthetic wearer, the wearer can significantly benefit.

The prosthetic device can also take advantage of a stance flexion which may allow the leg to absorb the shock at heel strike and store energy for release at the toe off. This may enable the rise of the center of gravity of the prosthesis user to be reduced which can prevent unnatural vaulting to occur. As a result of the decrease in the rise of the center of gravity of the wearer during each step, the energy consumption during walking and running can be greatly reduced.

At the end of the stance phase (toe-off), the energy can be effectively returned to the prosthesis user when the stored energy return is synchronized to the user's cadence. During the swing phase, lower variable resistance and compliance can be used. Furthermore, an extension assist can be used to help extend the knee mechanism.

Referring again to FIG. 2, a second vane 220 can extend outwardly from an opposing side of the rotary hub 216. The second vane can form a second chamber 213 in the joint housing 210 and the first opening leads to the second chamber via a second opening 215 in the joint housing. The second opening is in fluid communication with the first opening via a fluid passageway. The fluid passages allow the hydraulic fluid to pass through joint housing and other related support structures from first chamber to the second chamber and then back again (or through a separate return passageway) when the foot angle has changed relative to the prosthetic leg. For example, the second vane moves inside a second chamber with a second opening in the joint housing, and feeds a passageway which is not connected to the fluid passageway which feeds the first opening coming out of the first chamber.

The hydraulic fluid can be a silicone based fluid within the chamber that is in fluid communication with or direct contact with the vane(s). Alternatively, another viscous liquid or non-compressible working fluid can be used in conjunction with a compressible fluid such as air, or another substance in gaseous state.

A combination of hydraulic and/or pneumatic elements suitably arranged within a prosthetic system can facilitate concurrent damping and springing actions. The prosthetic system can be configured to cause a resistive action to the user through the dorsi-flexion stage. This resistive action contrasts with the freedom of motion felt through the planar flexion stage and facilitates the storage of bending energy in the toe keel, which is the component of the system supplanting a user's foot. Energy accumulation can be further subtended by a specifically defined curvature on the underside of a joint housing which allows the toe keel to undergo bending around its contours. The contours can be configured to increasingly resist the bending, leading to a ramped (though not necessarily linear) stiffness rise.

A sandwiched foam-like layer 240 may be placed in the keel to absorb shocks. An arrangement of compliant material comprising bushings which surround fasteners mounting the toe keel to the joint housing can isolate the user from ground contact-induced vibrations. In addition, a heel lever 231 can be disposed on a bottom of the joint housing, and the heel lever can be configured to absorb shock and transfer energy to the rotary hub.

A valve 224 (FIG. 2) is provided for controlling the fluid flow between the first opening and the second opening of the chamber. Other valves for the multiple fluid flow pathways can also be provided. The valve can be a manually adjustable valve, electronically controlled valve, or a weighted gravity valve.

The manually adjustable valve can be controlled by the amputee by twisting a knob 312, as in FIG. 3, that protrudes from the front the prosthetic foot. This allows the fluid resistance to be modified. A manual solution employs mechanical components, and also involves the passage of one or more working fluids. An aspect of this design may include a manual means for the user to be able to exercise periodic override control of the variable parameters of the device, as compared to the device acting only on internal electronic mechanisms for control.

An example of this involves adjustment of a damping factor for the fluid circuit governing plantar-flexion damping, and a separate similar adjustment of a damping factor for the fluid circuit governing dorsi-flexion damping. This can be achieved by the user who sets or resets of the position of one or several knobs and/or levers, which alters internal fluid circuit passage orifice diameter sizes, or varies a spring constant loading element which is part of a sub-circuit with an energy accumulation element.

Figure 4:
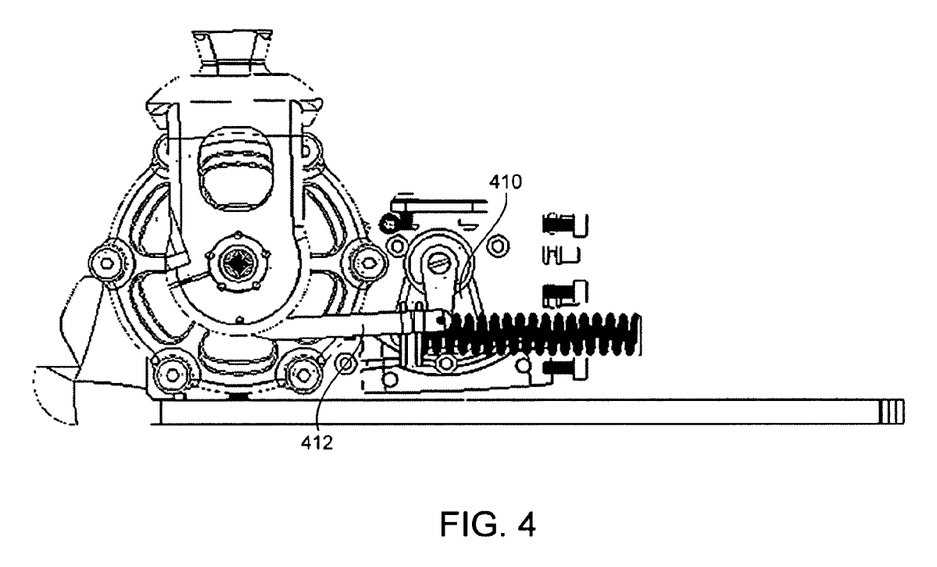
FIG. 4 is a side view of a prosthetic foot system with an electronically controlled hydraulic damping system.

FIG. 4 illustrates a valve that is controlled by a weighted gravity member, where a metal pendulum 410 or some other weighted object can be coupled to the valve. The pendulum member can be configured to control the fluid flow between the first opening and the second opening of the chamber in response to gravitational force, or to control fluid flow through fluid flow passages.

When the pendulum reaches a nearly vertical position then it can be configured to nearly close the valve and provide a high level of fluid resistance. For example, a smaller inner piece of the pendulum set can be configured to incrementally remain aligned with the direction of gravity, despite changes in the orientation of its larger surrounding valve partner member, which is directly linked to the joint base. In this case, the design relates to an ankle joint, and the base member may be the foot base-plate (or linked rigidly to that). While in the case of a knee joint, the base might be the amputee's socket which is fitted to the remnant femur section (or linked rigidly to that). A link arm 412 can also be included that connects the lower leg piece or pyramid mount bracket to an outer valve portion and the pendulum can be attached to an inner fluid valve piece. This positions the outer valve piece at the same angle as the pyramid mount bracket or lower leg piece.

Alternatively, in another gravity embodiment, this relationship may be inverted, whereby the artificial replacement for the tibia/fibula pair might be considered as the joint base for the knee. Irrespective of this, the pendulum might be supported on a shaft of relatively minor circumference as compared with its surrounding housing diameter to permit free swinging. The swinging is enhanced not simply by the virtue of a well-made bearing arrangement, but also taking advantage of a physical phenomenon whereby the efficiency of relative motion between elements is maximized by minimizing the circumferential surface area where the relative motion takes place.

In embodiments incorporating this style of the design, this rocking valve element controls the flow of the working fluid by causing certain fluid flow paths to become aligned either completely or partially in proportional amounts with each other. Other paths may be simultaneously shut off completely and/or partially to proportional degrees (and vice versa) at different positions of its motion, and may be immersed in a sealed housing containing a viscous fluid.

A quantity of fluid comprising the circuit working the vane actuator may be sectioned off from the main volume of working fluid. In fact, this volume of fluid may be one of entirely different physical characteristics to the main working fluid of the actuator circuit, since its purpose is primarily to surround the pendulum and provide some degree of damping to filter undesired aspects of the motion of the prosthesis or 'noise', such as joint member oscillations/vibrations above a certain frequency. A damping fluid may involve properties that are necessarily ideal for the function required of a transmission fluid which damps the forces generated during the stride of the amputee user. Thus, the damping fluid is likely to have a different composition from the fluid driven by the vanes.

Returning again to FIG. 2, a microprocessor 242 that is in communication with the electronic valve system can control the electronic valve using a servo-valve 224 and a brushless DC motor 226 to provide power to the servo-valve. The microprocessor can also control the valve and motor based on certain preconfigured algorithms. For example, the electronically controlled valve may variably control the fluid flow between the first opening and the second opening of the chamber to provide the fluid resistance that is desired for a certain portion of the amputees stance phase. The amount of fluid resistance can be controlled by a motor 226 which drives a gearbox 225 that opens and closes the valve.

As mentioned, the fluid flow passages associated with the actuator may be controlled by two or more servo-driven valves, which vary the main working fluid flow and provide the variably damped behavior for the prosthetic joint flexion motion. These valves act according to the control function of the element performing the tilt sensing function. Using an electrical charge, these valves may be driven by compact servo-motors, and act on amplified pulses sent to them by one or more microprocessors, which dictate power flow from one or more compact electrical storage elements. For example, power can be supplied by re-chargeable cells of a lithium-ion type housed within the vicinity of either joint or remotely elsewhere on the amputee and discretely connected by insulated leads.

As discussed before, more than one independent circuit can be provided for the working fluid to flow through. The path can commence at the chamber surrounding the vane, passing through at least one damping valve, then returning to the vane chamber. As to which of these paths is the active loop for the working fluid at any moment depends on the particular portion of gait motion which the joint is serving at that instant. While certain passage sections would be common, upon reversal of flow, the fluid might be guided down alternative paths by a series of one-way check valves, and over-pressure diverting valves with those parameters determining when to divert fluid. These diversions may be manually adjustable or electronically programmable.

Figure 5:
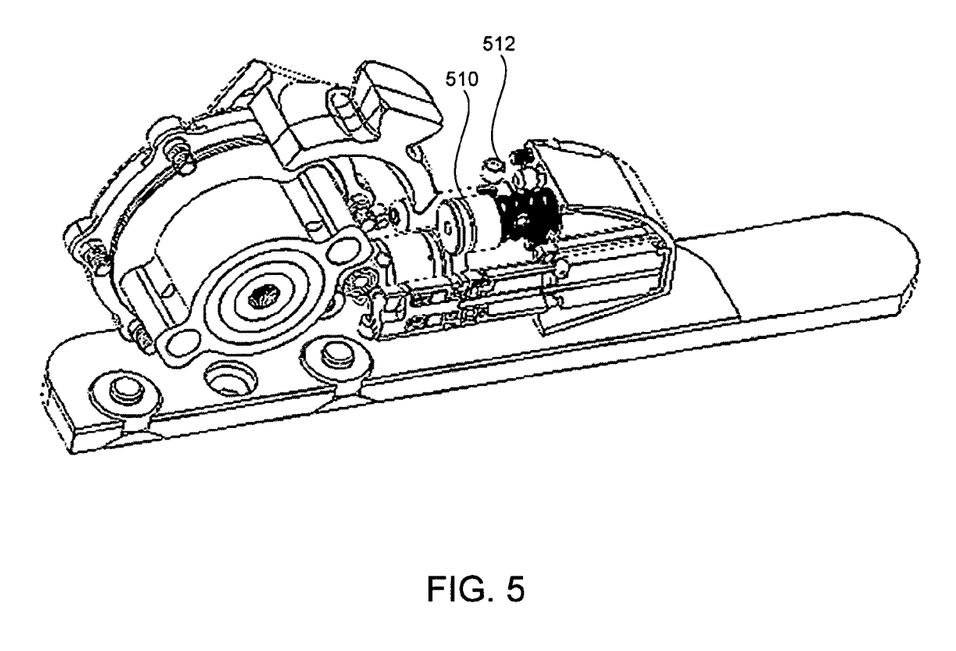
FIG. 5 illustrates a perspective cross-sectional side view of a prosthetic foot that also provides resistance to dorsi-flexion using a hydraulic and fluid storage system.

An additional feature of the present invention may incorporate a sub-circuit which stores some portion of the available energy constantly being generated in the fluid by the virtue of the work done on it by the amputee in undergoing stride motion in conjunction with gravity. This energy could be accumulated in the form of storage through compression of some suitable different fluid in a chamber, and/or compression of an elastic semi-rigid mechanical element. FIG. 5 illustrates a mechanical spring compression system 510 for storing such mechanical energy from the fluid. Another example is a bellow partially filled with oil and pressurized gas that is configured to store and return energy to an individual when the device is locked during a gait cycle.

At a particular instant in the stride of the user, from a timed release of this stored energy just described, the working fluid would be re-channeled back into the vane actuator, resulting in an assisted restoring action of the joint in (rotary) extension. This functionality might be implemented in either the ankle or knee joint, based on a user's customized requirements. Another useful function of an accumulator type sub-circuit is to constantly maintain the working fluid at a pressure elevated above atmospheric pressure, so that seals remain energized, thereby assisting with avoiding leakages.

Myoelectric sensors may be provided that are in communication with the microprocessor to control fluid impedance. The myoelectric sensor can sense changes in the amputee's skin and muscles, and then make appropriate changes in the impedance.

Another important sensor is an inclination sensing element 512, as in FIG. 5, that is in communication with the microprocessor. The fluid impedance can increase when the inclination sensing element determines that the amputee's leg prosthesis has reached the nearly vertical or completely vertical positions. Such measurements may be provided by the tilt and/or angulation sensor provided by a semi-conductor-based support circuitry package, which can continuously determine the direction of gravity and evaluate the changing orientation of critical elements of either joint in relation to gravity. Such a design may provide some functionality even when power is not available, or when power is suddenly lost without unduly compromising prosthetic functionality. The mechanically based circuit can default to a 'safe' mode of operation, which permits effective basic ambulation for the user.

Certain types of defined processing may also occur. The microprocessor may increase impedance when excessive plantar flexion or foot slapping occurs. In addition, the electronically controlled valve may control the dorsi-flexion and plantar-flexion impedances independently. Another example of processing that can aid the foot in moving properly is the calculation of the momentary cadence of the device.

In one embodiment, the present invention can provide for the capability of not only setting variables prior to commencement of motion, but can also permit these settings to be adjusted repeatedly during the cycles of the movement of each part of the mechanism, with the optional aid of an integrated microprocessor, according to pre-determined patterns, or according to manual over-ride choices made by the user in a less complex arrangement or mode of operation. Additional embodiments may employ a multi-faceted control algorithm which depends on a range of input variables, both user-customized and environmentally affected, and assisted by a look-up matrix, to enable more intelligent decision making.

A pressure relief valve 228 can be provided that is configured to release fluid pressure above a predefined pressure.

The joint housing 210 includes one or more stop-type structures 234a and 234b that can extend inwardly from the joint housing. The stopping structures may be configured to allow the one or two vanes to travel through at least 90 degrees of rotation within the chamber. In one embodiment, the vanes may travel through 104 degrees of rotation before they hit the stop structure.

In another embodiment of the present invention, the control system may utilize a microprocessor control system for myoelectric control of an electric prosthesis. This system has motor drivers appropriate for the motorized control valves on the proposed knee/ankle prosthesis. Furthermore, the computer user interface for setting control parameters can be used in the knee and/or ankle system. Such a system may allow for the control of:

1) Swing phase impedance by varying flexion and extension valves,

2) Flexion impedance and flexion locking via flexion valve, and

3) Stance phase compliance by a changing gas spring valve.

In an embodiment of the present invention, the foot/ankle may travel an approximate total of 88 degrees, comprising 55 degrees of plantar flexion and 33 degrees of dorsi-flexion. There may, be other values from these characteristics which may be seen as more or less useful, depending on the needs of the amputee.

The plantar/dorsi flexion axis may be at an angle other than 90 degrees from the vertical to approximate the axis of the intact human ankle. This allows proper rotation of the foot during the stance phase of gait.

Additionally, the compliant mount between the hydraulic actuator and energy storing foot can allow 10 degrees abduction of the foot and 10 degrees adduction, though there may also be other desired values for these parameters, depending on the needs of the amputee. Furthermore, the compliant mount will allow 10 degrees of inversion and 10 degrees of eversion, though a different embodiment of the same invention may permit greater or lesser values of these settings, since such parameters are not the focal concern of this invention. At the onset of stance phase-heel strike, the hydraulic knee mechanism may lock to prevent knee buckling, but allow up to about 20 degrees of compliant (springy) flexion.

Figure 6:
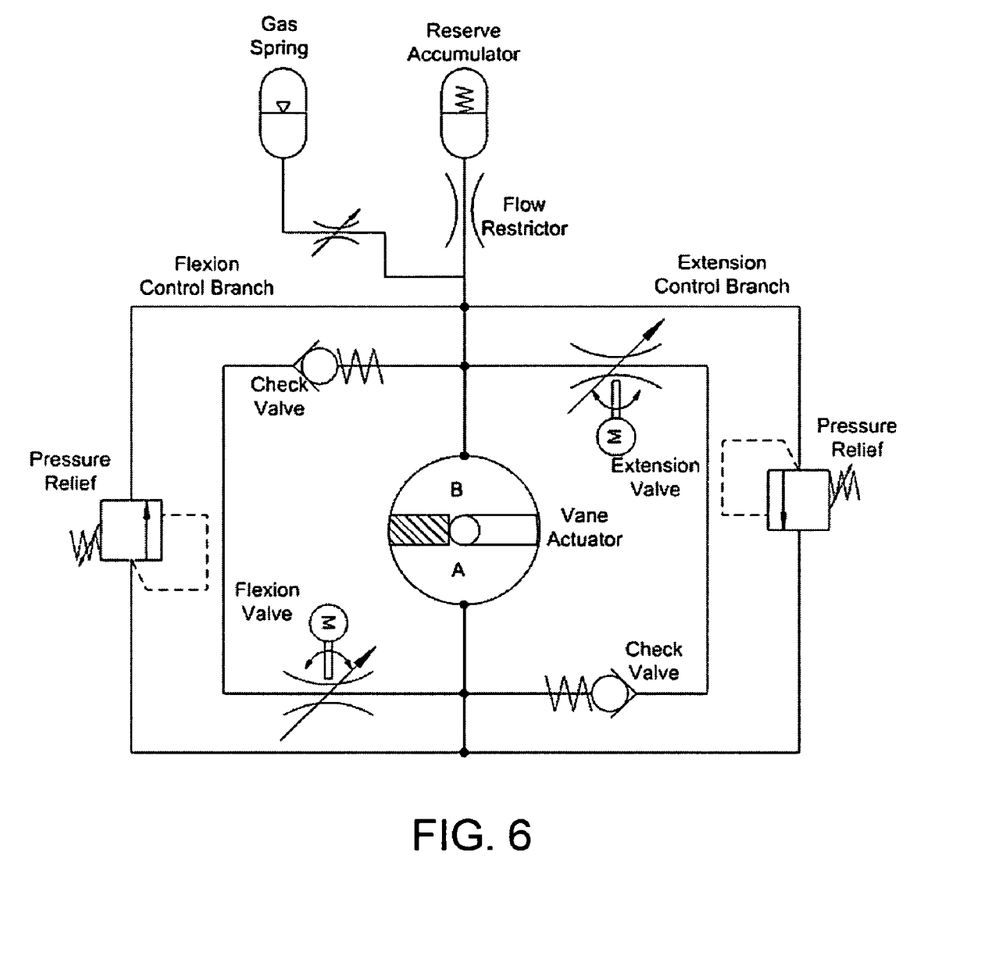
FIG. 6 is a schematic diagram of a fluid flow system for a hydraulic damping system in an embodiment of the present invention.

Referring to FIG. 6, a fluid flow schematic is illustrated that represents one embodiment of the invention. There are also various components for performing necessary secondary functions on the working fluid of such a joint. These components include electrically operated valves for flow restriction, over-pressure relief, single direction flow checking, as well as a reservoir for fluid accumulation and passage seals, amongst others.

Figure 8:
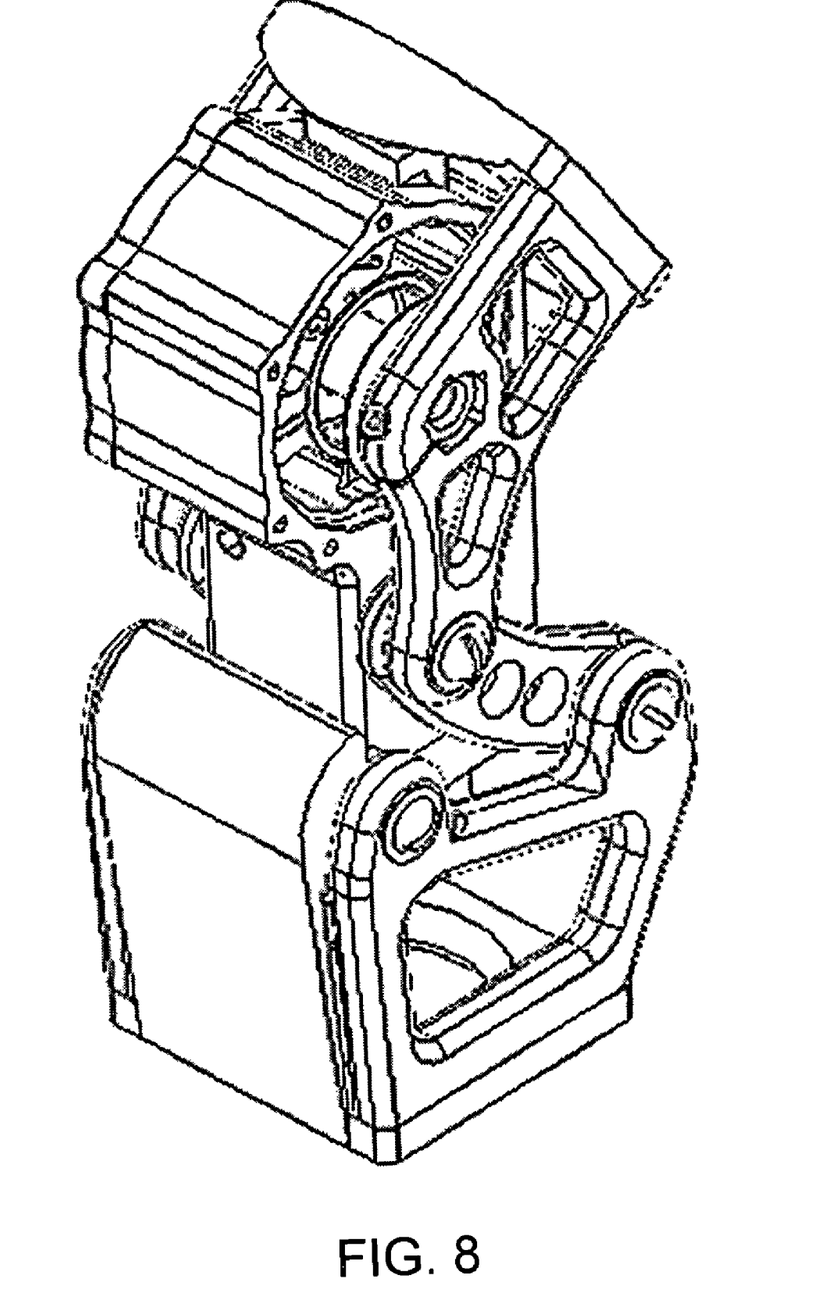
FIG. 8 is a perspective view of a prosthetic knee with an electronically controlled hydraulic damping system in an embodiment of the invention.

FIG. 8 illustrates that the prosthetic system can be implemented in a transfemoral knee/ankle prosthesis, allowing disabled individuals with lower limb deficiencies to walk and run more smoothly, with more stability, and with less effort, thereby, allowing them to live more productive and enriched lives. Furthermore, this proposed prosthetic device will enable individuals with lower limb deficiencies to engage in activities which currently available devices do not allow. FIG. 8 specifically illustrates a perspective view of a knee using the hydraulic vane actuator as described for the ankle. The knee system can use similar systems for the motors, valves, fluid conduits, while accounting for changes in orientation and actual usage. In one embodiment, the prosthetic system can be comprised of four main elements: 1) a knee mechanism, 2) an ankle mechanism, 3) knee/ankle frame/linking components, and 4) a controller configured to simultaneously control both devices.

The knee joint mechanism consists of a hydraulic cylinder which extends when the knee extends and contracts as the knee flexes. The resistance to extension and the resistance to flexion of the valve can be modulated independently via two miniature electrically powered D.C. motors, which can rapidly position and re-position internal components of such a valve, according to settings made manually or to commands received in a signal stream from an integral controller coupled to the motors. The integral controller can be a microprocessor.

The ankle mechanism, likewise, is comprised of one or more hydraulic cylinders. The hydraulic cylinders can be placed side by side, or closely stacked. These cylinders extend as the ankle dorsi-flexes, and contract when the ankle plantar-flexes. The resistance for each set of cylinders can be variably controlled by a motor-driven hydraulic valve, wherein the valve is configured to alter the volume and pressure of the working fluid.

In one embodiment of such an ankle or knee joint, piston dampers acting linearly can be the means of providing a variable stiffness and damping characteristic, permitting a relatively low profile which can be advantageous. In a second embodiment, a vane-like damper/actuator can be employed, which accommodates for a larger range of motion.

An additional embodiment may include microprocessor hardware locally located at each of the two separate ankle/knee joint locations. These microprocessors can be networked together or wireless connected to provide a means of active communication between the microprocessors. For example, a constant relay of the instantaneous angular positions associated with the foot can be transmitted to the knee unit. This data can describe not only the angle between the primary members of the ankle joint, but also the relative orientation to the tread surface, and further still the surface inclination. This information allows the impedance of the knee joint's flexion/extension action to be instantaneously set and reset according to gait requirements as determined by population statistical norms or according to individual amputee particularities.

When the present device is applied to a knee joint, than a four bar linkage mechanism can be used. During flexion, the locus shift of its polycentric characteristic positions the center of mass in a favorable manner such that it rises, and locates itself more and more anterior to the vertical line of action of the tibia/fibula pylon. This provides a counter-moment to buckling at the knee and assists the user in maintaining a more stable stance than that generally associated with designs involving fixed pivot centre distances Also during its flexion, action of the mechanism around the knee joint leads to a foreshortening of the effective length of the member(s) connecting to the ankle joint, and this aids the user in avoiding tripping. Since the knee joint may be communicatively linked with the ankle joint, the ankle joint might be synchronized to orient itself in maintaining maximum dorsi-flexion from the commencement of swing phase through to at least halfway towards heel contact. This configuration can assist in maximizing the distance between the lowest point of the prosthesis and the floor (equivalent to clearance between ground and where the big toe would otherwise be), and can maximize the convenience and safety of the amputee.

Figure 9:
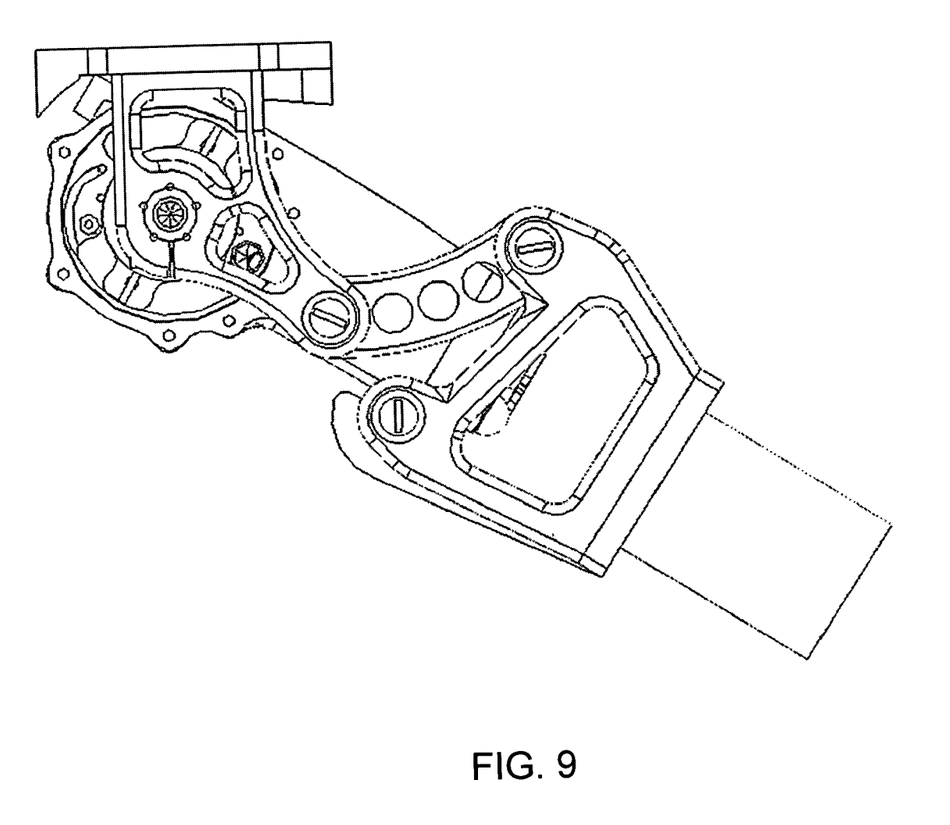
FIG. 9 is a side orthogonal view of a prosthetic knee with an electronically controlled hydraulic damping system in an embodiment of the invention.

FIG. 9 illustrates a side view of the four bar linkage. In addition, the housing on the hydraulic cylinder has been removed and the rotary hub and vane can be seen inside the hydraulic knee.

Figure 7:
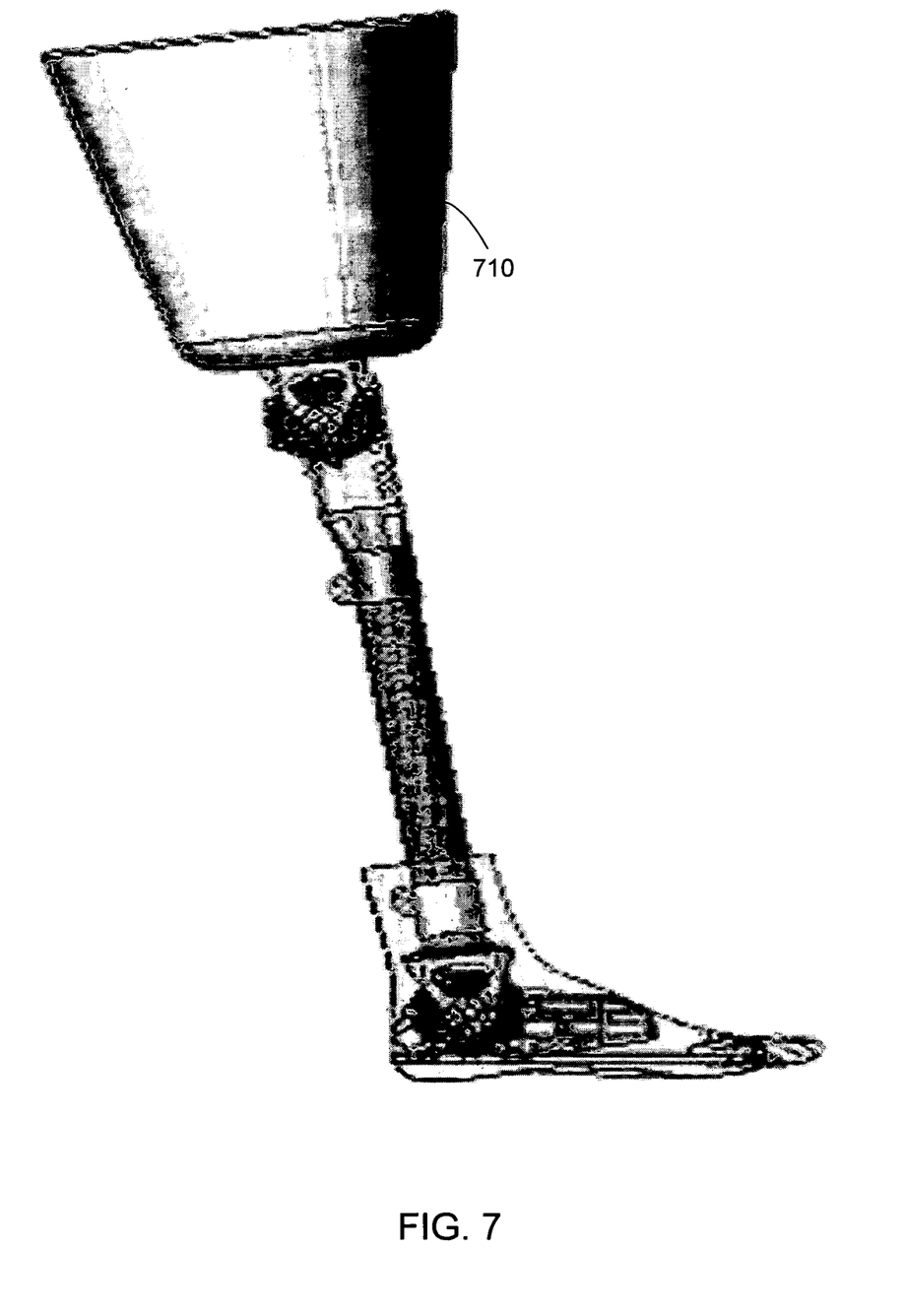
FIG. 7 is a side view of an amputee's lower limb configuration in an above-knee joint amputation.

In another embodiment, a device 710, as shown in FIG. 7, may be used to replace the wearer's lower limb set in an above-knee joint amputation, though there may be other circumstances in which the device may be employed both in its whole integral format as described herein, or used in part, such as in the prosthetic replacement of just an ankle joint, or just a knee joint alone. The device may connect to current prosthetic components either within or beyond the envelope framed by the combined ankle and knee joints, either together or separately, using a standard pyramid boss/socket arrangement. Other means of connectivity may also be suitably employed.

There exist three 'rockers' or rocker stages defining the stages of a user's stance phase in ambulation, requiring particular design attention to obtain response behavior for an effective lower limb prosthetic solution. An example of how the present invention is beneficial to an amputee will be described as related to the stance or rocker phases of ambulation.

The first rocker phase includes travel with a flat down in plantar flexion. Immediately subsequent to the heel strike, there is absorption of shock of the user's combined momentum due to forward momentum imparted and/or gravity imparted motion achieved by controlled hydraulic resistivity in the relative rotational motion between members of the ankle joint during its flexion. The use of hydraulic resistance overcomes the need for linear shock absorption which in the prior art may be housed in the artificial replacement for the tibia/fibula. Thus, foreshortening of the limb is desirably avoided, as contrasted with the prior art where the necessary accompanying restoring linear extension persistently presents a challenge for the user not to stumble.

The second rocker phase includes transition from plantar flexion to dorsi-flexion. This phase is also a period during which shock absorption is taking place, and similarly is achieved by controlled resistivity in the relative rotational motion between members of the ankle joint during flexion. However, in contrast to the relative motion during the first rocker phase, this is in the opposite direction. As a result, this flow reversal of the working fluid is handled most effectively by passage through an entirely separate circuit than that passage intended for flow during the first rocker phase. Using a separate fluid passage enables intensity and rate characteristics in the present invention which overcome the contrasting requirements between the two different motion regimes.

The third rocker phase includes the on transition to toe-off portions. Prior to commencement of the swing phase from culmination of stance phase, there is onset of a damping action at the knee joint. Variable factors include the point of termination being the instant of knee joint locking This locking point may be at the instant the limb is in vertical orientation during the stance phase or slightly sooner or later than absolute vertical depending on the usage demands. For example the point of termination may vary depending on:

whether travel is up-hill, down-hill, or across a flat surface, or whether stride is intended to be walking or running Locking of the knee joint prepares for the necessary ground-force reaction experienced at toe-off, instigating the swing phase.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A prosthetic device having an articulating ankle joint for a leg amputee, comprising:
    a joint housing forming a first chamber, the first chamber having a first opening;
    a rotary hub disposed within the joint housing, movable independently of the joint housing, and wherein the rotary hub is the articulating joint;
    a plurality of vanes integrally formed with and extending radially symmetrically outwardly from the rotary hub, the plurality of vanes comprising a first vane and a second vane, the second vane being located on an opposing side of the rotary hub directly opposite the first vane, wherein the vanes are fully enclosed within the joint housing, and wherein at least one of the plurality of vanes is configured to rotate and actuate fluid flow through the first opening; and
    a toe keel element mounted on a spherical or cylindrical surface of the joint housing in order to facilitate resistance to eversion and inversion.

2. A device as in claim 1, further comprising:
    a second opening to the first chamber of the joint housing, configured to be in fluid communication with the first opening;
    a valve for controlling the fluid flow between the first opening and the second opening of the chamber, wherein the valve is self-adjustable during use.

3. A device as in claim 2, wherein the valve is selected from a group consisting of an electronically controlled valve, and a weighted gravity valve.

4. A device as in claim 3, wherein the weighted gravity valve incorporates a pendulum motion action.

5. A device as in claim 1, wherein the second vane moves inside a second chamber in the joint housing and the first opening leads to the second chamber via a second opening and fluid passageway in the joint housing.

6. A device as in claim 1, further comprising a pressure relief valve, coupled to the fluid flow and configured to divert fluid flow when fluid pressure exceeds a predefined pressure value.

7. A device as in claim 1, wherein the toe keel element is directly coupled to a bottom side of the joint housing with a single pivot point coupling, to allow rotation about the axis of the device.

8. A device as in claim 1, further comprising an elastomeric heel element directly coupled to the joint housing to provide shock absorption during a heel strike.

9. A device as in claim 1, further comprising a bellow partially filled with oil and pressurized gas to store and return energy to an individual when the prosthetic device is locked during a gait cycle.

10. A device as in claim 1, further comprising air as a working fluid within the first chamber and in fluid communication with at least one of the plurality of vanes.

11. A device as in claim 1, wherein the toe keel element is directly coupled to the joint housing and stores and releases energy during a third rocker phase of a stance gait cycle, wherein the third rocker phase includes an on transition to toe-off portions of the stance gait cycle.

12. A device as in claim 1, further comprising a heel lever disposed on a bottom of the joint housing to absorb shock and transfer energy to the rotary hub.

13. A device as in claim 1, wherein the joint housing includes a stopping structure extending inwardly from the joint housing to allow at least one of the plurality of vanes to travel through at least 90 degrees of rotation within the first chamber.

14. A prosthetic ankle device for a leg amputee having hydraulic resistance, comprising:
   a joint housing having a first chamber, the first chamber having a first opening, and a second opening in fluid communication with the first opening;
   a rotary hub disposed within the joint housing, movable independently of the joint housing, and wherein the rotary hub is an articulating joint;
   a plurality of vanes integrally formed with and extending radially symmetrically outwardly from the rotary hub, the plurality of vanes comprising a first vane and a second vane, the second vane being located on an opposing side of the rotary hub directly opposite the first vane, wherein the vanes are fully enclosed within the joint housing, and wherein at least one of the plurality of vanes is configured to rotate and actuate fluid flow through the first opening;
   a valve for controlling the fluid flow between the first opening and the second opening of the first chamber; and
   a toe keel element mounted on a spherical or cylindrical surface of the joint housing in order to facilitate resistance to eversion and inversion.

15. A prosthetic device as in claim 14, wherein the valve is a manually operated control.

16. A prosthetic device as in claim 14, wherein the second vane forms a second chamber in the joint housing and the first opening leads to the second chamber.

17. A prosthetic device for a leg amputee having at least one ankle joint, comprising:
   a joint housing having a first chamber, the first chamber having a first opening and a second opening in fluid communication with the second opening;
   a rotary hub having a plurality of vanes integrally formed radially symmetrically therewith and fully enclosed within the joint housing, the rotary hub being disposed within the joint housing and movable independently of the joint housing, wherein the rotary hub is an articulating ankle joint, and wherein the plurality of vanes are configured to rotate and actuate fluid flow and comprise a first vane and a second vane, the second vane being located on an opposing side of the rotary hub directly opposite the first vane; and
   an electronically controlled valve for variably controlling the fluid flow between the first opening and the second opening of the first chamber.

18. A device as in claim 17, further comprising a microprocessor in communication with the electronic valve to control the electronic valve based on a preconfigured algorithm.

19. A device as in claim 17, further comprising an inclination sensing element in communication with the microprocessor.

20. A device as in claim 17, wherein the microprocessor can increase impedance when excessive plantar flexion occurs.

21. A device as in claim 17, where in the microprocessor calculates a momentary cadence of the device.

22. A device as in claim 17, wherein the electronically controlled valve is a servo-valve, and the device further comprises a brushless DC motor to provide power to the servo-valve.

23. A device of claim 17, wherein the electronically controlled valve controls dorsi-flexion and plantar-flexion impedances independently.

* * * * *